US010555736B2

(12) United States Patent
Machold et al.

(10) Patent No.: US 10,555,736 B2
(45) Date of Patent: Feb. 11, 2020

(54) GUIDEWIRE

(71) Applicant: PneumRx, Inc., Santa Clara, CA (US)

(72) Inventors: Timothy Machold, Moss Beach, CA (US); Mark Mathis, Fremont, CA (US); Verna Rodriguez, Santa Cruz, CA (US); Scott Kaarto, Santa Clara, CA (US)

(73) Assignee: PneumRx, Inc., Santa Clara, CA (US)

(*) Notice: Subject to any disclaimer, the term of this patent is extended or adjusted under 35 U.S.C. 154(b) by 307 days.

(21) Appl. No.: 15/719,792

(22) Filed: Sep. 29, 2017

(65) Prior Publication Data

US 2018/0092647 A1 Apr. 5, 2018

Related U.S. Application Data

(60) Provisional application No. 62/402,852, filed on Sep. 30, 2016.

(51) Int. Cl.
*A61B 17/12* (2006.01)
*A61M 25/09* (2006.01)

(52) U.S. Cl.
CPC .. *A61B 17/12104* (2013.01); *A61B 17/12031* (2013.01); *A61M 25/09* (2013.01);
(Continued)

(58) Field of Classification Search
CPC ........ A61B 17/12031; A61B 17/12104; A61B 2017/1205; A61M 2025/09083;
(Continued)

(56) References Cited

U.S. PATENT DOCUMENTS 4,773,432 A 9/1988 Rydell
4,917,102 A 4/1990 Miller et al.
(Continued)

FOREIGN PATENT DOCUMENTS

WO 2009020836 2/2009

OTHER PUBLICATIONS

PneumRx Lung Volume Reduction Devices (LVRD) Instructions for Use, 2007, 8 pages.

(Continued)

*Primary Examiner* — Ryan J. Severson
*Assistant Examiner* — Mohamed G Gabr
(74) *Attorney, Agent, or Firm* — Kilpatrick Townsend & Stockton LLP

(57) ABSTRACT

Guidewires suitable for use in a system for implanting a lung volume reduction device are disclosed. The guidewire includes an outer sheath having proximal and distal ends, and comprising a proximal section, a transition section, and a distal section. The proximal section extends from the proximal end of the sheath to the transition section, and the distal section extends from the transition section to the distal end of the sheath. The distal section defines a bore extending from the transition section to the distal end of the sheath and an inner core having proximal and distal ends. The inner core extends through the bore of the distal section of the sheath, wherein the inner core is fixed to the sheath at the transition section, and wherein the distal end of the inner core is fixed to the distal end of the sheath at the distal end of the sheath.

22 Claims, 9 Drawing Sheets

42 48 50 52 61

56 62 60 42 64

(52) U.S. Cl.
CPC ................ *A61B 2017/1205* (2013.01); *A61M 2025/09083* (2013.01); *A61M 2025/09175* (2013.01); *A61M 2210/1039* (2013.01)

(58) Field of Classification Search
CPC ......... A61M 2025/09166; A61M 2025/09175; A61M 2210/1039; A61M 25/09
USPC .......................................................... 600/585
See application file for complete search history.

(56) References Cited

U.S. PATENT DOCUMENTS 5,054,501 A 10/1991 Chuttani et al.
5,333,620 A 8/1994 Moutafis et al.
5,365,943 A * 11/1994 Jansen .................. A61M 25/09 600/585
5,409,015 A * 4/1995 Palermo ................ A61M 25/09 600/585
6,174,323 B1 1/2001 Biggs et al.
6,183,420 B1 2/2001 Douk et al.
6,287,290 B1 9/2001 Perkins et al.
6,371,928 B1 4/2002 Mcfann et al.
6,398,775 B1 6/2002 Perkins et al.
6,409,682 B1 6/2002 Burmeister et al.
6,459,921 B1 10/2002 Belef et al.
6,514,290 B1 2/2003 Loomas
6,527,761 B1 3/2003 Soltesz et al.
6,599,311 B1 7/2003 Biggs et al.
6,669,652 B2 12/2003 Anderson et al.
6,709,401 B2 3/2004 Perkins et al.
6,712,812 B2 3/2004 Roschak et al.
6,716,183 B2 4/2004 Clayman et al.
6,878,141 B1 4/2005 Perkins et al.
6,929,637 B2 8/2005 Gonzalez et al.
6,997,189 B2 2/2006 Biggs et al.
6,997,918 B2 2/2006 Soltesz et al.
7,115,101 B2 10/2006 Cornelius et al.
7,141,046 B2 11/2006 Perkins et al.
7,175,644 B2 2/2007 Cooper et al.
7,186,259 B2 3/2007 Perkins et al.
7,458,963 B2 12/2008 Perkins et al.
7,468,350 B2 12/2008 Gong et al.
7,549,984 B2 6/2009 Mathis
7,553,810 B2 6/2009 Gong et al.
7,595,082 B2 9/2009 Connors, III et al.
7,608,579 B2 10/2009 Gong et al.
7,662,181 B2 2/2010 Deem et al.
7,670,282 B2 3/2010 Mathis
7,678,767 B2 3/2010 Gong et al.
7,717,115 B2 5/2010 Barrett et al.
7,766,938 B2 8/2010 McGurk et al.
7,775,968 B2 8/2010 Mathis
7,883,474 B1 2/2011 Mirigian et al.
7,932,225 B2 4/2011 Gong et al.
7,942,931 B2 5/2011 Gonzalez et al.
8,142,455 B2 3/2012 Thompson et al.
8,157,823 B2 4/2012 Aronson et al.
8,157,837 B2 4/2012 Thompson et al.
8,282,660 B2 10/2012 Thompson et al.
8,431,537 B2 4/2013 Gong et al.
8,632,605 B2 1/2014 Thompson et al.
8,668,707 B2 3/2014 Thompson et al.
8,721,734 B2 5/2014 Mathis et al.
8,888,800 B2 11/2014 Mathis et al.
8,911,465 B2 12/2014 Mathis et al.
8,932,310 B2 1/2015 Thompson et al.
9,125,639 B2 9/2015 Mathis et al.
9,173,669 B2 11/2015 Mathis et al.
9,192,403 B2 11/2015 Aronson et al.
9,402,632 B2 8/2016 Mathis et al.
9,402,633 B2 8/2016 Vasquez et al.
RE46,209 E 11/2016 Gong et al.
2005/0281739 A1 12/2005 Gong et al.
2005/0281740 A1 12/2005 Gong et al.
2005/0281796 A1 12/2005 Gong et al.
2005/0281798 A1 12/2005 Gong et al.
2005/0281799 A1 12/2005 Gong et al.
2005/0281800 A1 12/2005 Gong et al.
2005/0288684 A1 12/2005 Aronson et al.
2005/0288702 A1 12/2005 McGurk et al.
2006/0004400 A1 1/2006 McGurk et al.
2006/0025815 A1 2/2006 McGurk et al.
2008/0021405 A1 1/2008 Jacobsen et al.
2008/0312543 A1 12/2008 Laufer et al.
2009/0131765 A1 5/2009 Roschak et al.
2010/0297218 A1 11/2010 Gong et al.
2012/0265100 A1 10/2012 Maki
2013/0096603 A1 4/2013 Mathis et al.
2013/0103059 A1 4/2013 Mathis et al.
2013/0184579 A1 7/2013 Roschak et al.
2014/0073588 A1 3/2014 Gong et al.
2014/0371705 A1 12/2014 Thompson et al.
2015/0073563 A1 3/2015 Mathis et al.
2015/0080934 A1 3/2015 Aronson et al.
2015/0119920 A1 4/2015 Mathis et al.
2015/0142035 A1 5/2015 Mathis et al.
2015/0328435 A1 11/2015 Mathis et al.
2016/0113657 A1 4/2016 Mathis et al.
2017/0027584 A1 2/2017 Vasquez et al.
2017/0027585 A1 2/2017 Mathis et al.
2017/0065282 A1 3/2017 Mathis et al.
2017/0156732 A1 6/2017 Lehrberg et al.
2018/0028193 A1 2/2018 Mathis et al.
2018/0064411 A1 3/2018 Roschak et al.

OTHER PUBLICATIONS

PneumRx RePneu Coil System Instructions for Use, Dec. 2014, pp. 1-8.
PneumRx RePneu Lung Volume Reduction Coil (LVRC) Instructions for Use, 2010, pp. 1-8.
PneumRx RePneu Lung Volume Reduction Coil (LVRC) System Instructions for Use, Jun. 2015, pp. 1-8.
PneumRx, Inc., 3 Marker Guidewire Assembly schematics, drawn by D. Lehrberg, 2011, 1 page.
PneumRx, Inc., Guidewire Core Wire and Guidewire Coil schematics, drawn by D. Lehrberg, 2010, 2 pages.
PneumRx, Inc., Introducer RO Coil schematics, drawn by P. Wu, 2007, 1 page.
PneumRx, Inc., RePneu Lung Volume Reduction Coil (LVRC) System Instructions for Use, Feb. 2014, pp. 1-8.

* cited by examiner

GUIDEWIRE

CROSS REFERENCE TO RELATED APPLICATIONS

The present application claims the benefit of U.S. Provisional Application Ser. No. 62/402,852, filed on Sep. 30, 2016, which is incorporated by reference herein in its entirety for all purposes.

BACKGROUND OF THE INVENTION

The invention relates to guidewires suitable for use in the deployment of implants for lung volume reduction.

In chronic obstructive pulmonary disease, damage to tissue in certain parts of the lungs means that normal muscular inflation and deflation of the lungs becomes less efficient. One method to improve this situation is lung volume reduction, in which the diseased tissue is compressed or collapsed so that the remaining tissue can behave more normally. In one form of lung volume reduction, one or more elongate spring implants are deployed into the airways in the diseased lung tissue and are allowed to contract, gathering up the diseased tissue as they do so. Implants and systems for such treatments are disclosed in WO 2007/106495 and WO 2010/030993. In both cases, implants are deployed into the airways from catheter systems. The airways of the lungs are highly branched and tortuous, and lung tissue can be easily damaged. Therefore guidewires are used to determine the path to the airway to be treated, the catheter for delivery of the implant being advanced over the guidewire, which is then removed so that the implant can be deployed through the properly positioned catheter.

The guidewire must be capable of being pushed out of the catheter and into airway, and rotated so that it advances in the desired direction, while at the same time being small enough that the delivery catheter can fit over it to be advanced into the lung for proper delivery of the implant. In order to reduce the likelihood of kinking due to the combination of compression and torsion, a composite structure has been proposed for the guidewire, comprising an inner core extending through an outer coil sheath. In order to allow the guidewire to be advanced through the catheter, the proximal part of the core is relatively thicker than the distal part, which is thinner to provide the necessary flexibility to be directed through the airways without damaging the lung tissue. One result of this is that applying torque at the proximal end of the guidewire to steer the distal end in the required direction can result in significant wind-up between the core and coil, making accurate control of the distal end difficult.

The invention attempt to address the problem of how to provide more accurate control of the distal end while retaining the necessary flexibility in the system.

SUMMARY

The various aspects of the present invention relate to improved guidewires for use in deployment of lung volume reducing implants, such as coils. One aspect provides a guidewire, comprising: an outer sheath having a proximal end and a distal end, and comprising a proximal section, a transition section, and a distal section, wherein the proximal section extends from the proximal end of the outer sheath to the transition section, and the distal section extends from the transition section to the distal end of the outer sheath, and wherein the distal section defines a bore extending from the transition section to the distal end of the outer sheath; and an inner core having a proximal end and a distal end, wherein the inner core extends through the bore of the distal section of the outer sheath, wherein the inner core is fixed to the outer sheath at the transition section, and wherein the distal end of the inner core is fixed to the distal end of the outer sheath at the distal end of the sheath.

By fixing the inner core to the outer sheath at the transition section, it is not necessary for the core to extend the whole length of the sheath and so allows different physical properties to be provided for the proximal and distal sections of the sheath.

In one configuration, the proximal section of the outer sheath defines a bore extending from the proximal end of the sheath to the transition section. In this case, the bore of the proximal section of the outer sheath can be substantially unobstructed between the proximal end of the sheath and the transition section.

The proximal section of the outer sheath and the distal section of the outer sheath can comprise coils. In this case, the coil comprising the proximal section of the outer sheath can have different mechanical properties to the coil comprising the distal section of the outer sheath. For example, the proximal section can be configured to apply torque to the transition section and distal section, and the distal section can be configured for flexibility.

The transition section can comprise an adapter to which the coils comprising the proximal and distal sections of the outer sheath are fixed. In one example, the transition section comprises a cylindrical body having a proximal pin extension for insertion into and fixture to an open end of the coil comprising the proximal section of the outer sheath, and a distal pin extension for insertion into and fixture to an open end of the coil comprising the distal section of the outer sheath, the distal pin extension also comprising a bore for receiving and fixing the inner core. This configuration allows a substantially constant outer diameter across the transition section and so helps avoid snagging.

The proximal end of the inner core can be fixed to the outer sheath at the transition section. The distal end of the outer sheath and the distal end of the inner core can be fixed to a ball structure. Thus the end of the structure can have a atraumatic shape and so avoid damage to lung tissue as it is advanced.

The inner core can comprise a wire having a flattened portion intermediate the proximal and distal ends. The proximal and distal ends of the wire can have substantially the same diameter. This allows modification from a simple wire structure to provide a core that preferentially bends in one plane, assisting in directing the guidewire though lung airways.

The outer sheath is dimensioned to pass through a catheter for introduction into an airway of the lung of a patient.

The guidewire can further comprise an end fitting connected to the proximal end of the proximal section and configured to allow a user to apply torque to the proximal section. The end fitting can comprise a hub that is permanently or removably connected to the proximal end of the proximal section.

Another aspect provides a system comprising a first catheter, a guidewire as defined above, and a second catheter, wherein the first catheter is configured for introduction into the major airways of the lung of a patient, the guidewire is configured to be advanced from a lumen of the first catheter and further into a predetermined airway in the lung of the patient, and the second catheter is configured to be advanced through the lumen of the first catheter and over the guidewire into the predetermined airway of the lung of the patient. The system can further comprise an implant configured for delivery through a lumen in the second catheter and deployment into the predetermined airway of the lung of the patient.

Another aspect provides method of deploying a lung volume reduction implant into a predetermined airway of a lung of a patient, comprising advancing the first catheter and the guidewire into a major airway of the lung; advancing the second catheter and guidewire through the lumen of the first catheter; advancing the guidewire from the lumen of the second catheter and directing the distal end of the guidewire further into the predetermined airway by rotating the proximal end of the outer sheath so as to point the distal end of the outer sheath in the direction of the predetermined airway; withdrawing the guidewire from the second catheter; and advancing a lung volume reduction implant through the lumen of the second catheter and deploying the implant into the predetermined airway.

Another aspect provides a system comprising: a first catheter configured for introduction into the major airways of the lung of a patient; a second catheter configured to be advanceable through the lumen of the first catheter and further into a predetermined airway in the lung of the patient; and a guidewire according to any preceding aspects and configured to be advanced through a lumen of the second catheter and further into the predetermined airway, wherein the second catheter is configured to be further advanceable over the guidewire and further into the predetermined airway of the lung of the patient. The system can further comprise an implant configured for delivery through a lumen in the second catheter and deployment into the predetermined airway of the lung of the patient.

Another aspect provides a method of deploying a lung volume reduction implant into a predetermined airway of a lung of a patient, comprising: advancing the first catheter into a major airway of the lung; advancing the second catheter and guidewire through the lumen of the first catheter so as to extend into a predetermined airway of the lung; further advancing the guidewire from the lumen of the second catheter and directing the distal end of the guidewire further into the predetermined airway by rotating the proximal end of the outer sheath so as to point the distal end of the outer sheath in the direction of the predetermined airway; further advancing the second catheter over the guidewire further into the predetermined airway; withdrawing the guidewire from the second catheter; and advancing a lung volume reduction implant through the lumen of the second catheter and deploying the implant into the predetermined airway.

Other aspects of the invention will be apparent from the following description.

DETAILED DESCRIPTION OF THE INVENTION

Figure 1:
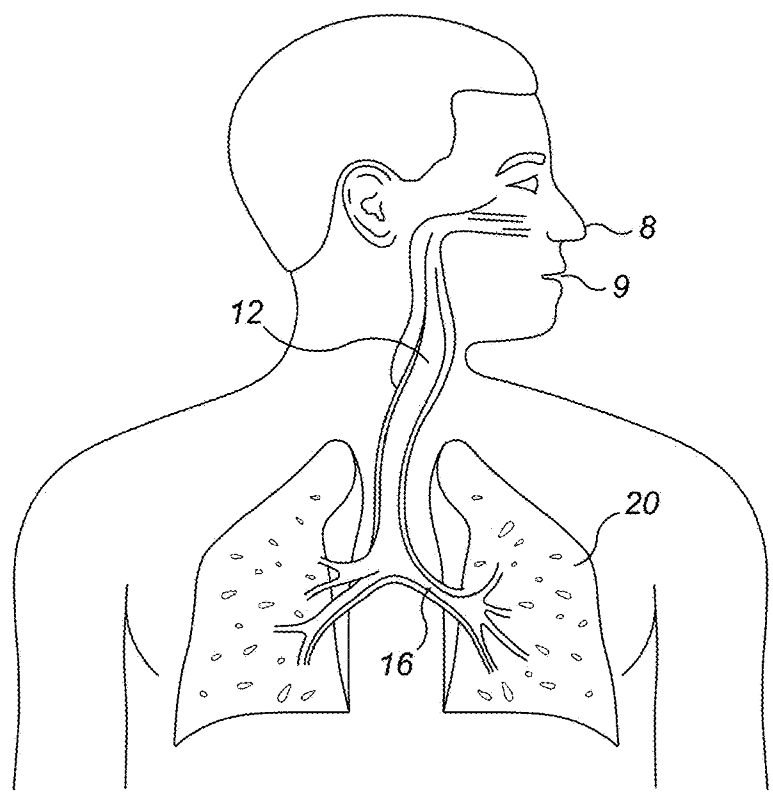
FIGS. 1 and 2 illustrate the human respiratory system.
Figure 2:
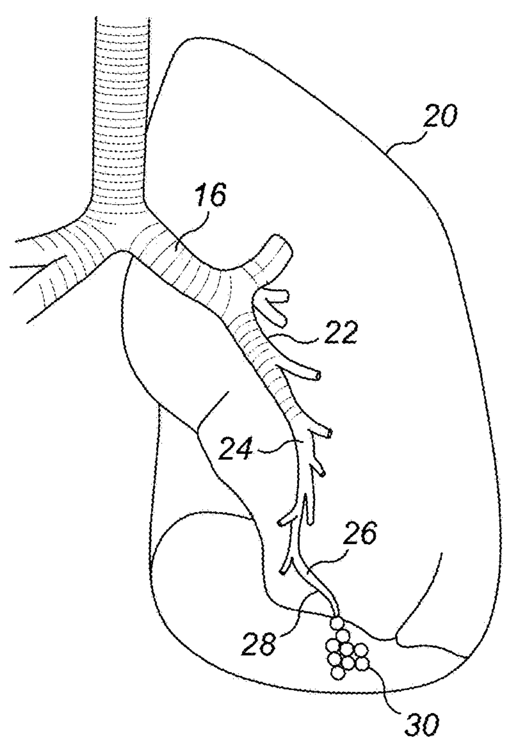

FIGS. 1 and 2 illustrate the human respiratory system, including the trachea 12, which directs air from the nose 8 or mouth 9 into the primary bronchus 16. Air enters the lung 20 from the primary bronchus 16. As is shown in FIG. 2, the primary bronchus 16 branches into the secondary bronchus 22, tertiary bronchus 24, bronchioles 26, terminal bronchioles 28, and finally into the alveoli 30.

Figure 3:
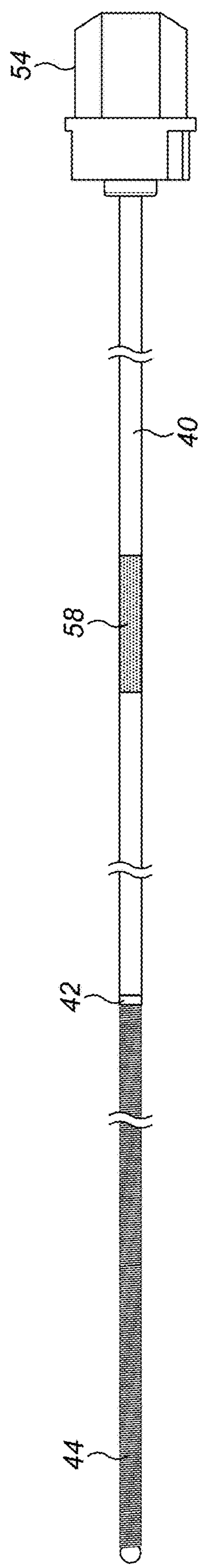
FIG. 3 shows an example of a guidewire.
Figure 4:
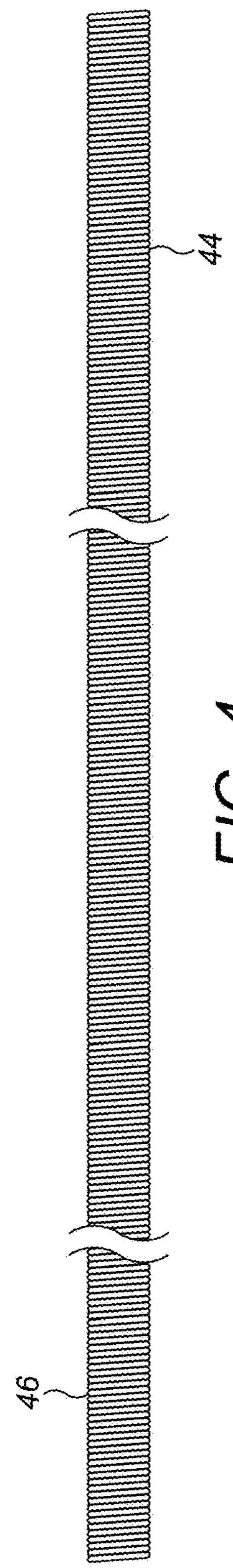
FIG. 4 shows further detail of the distal end of the outer sheath.
Figure 5:
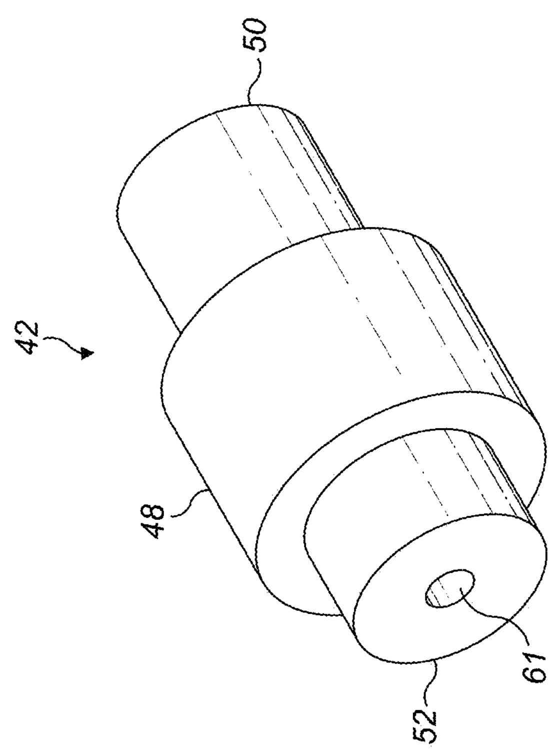
FIG. 5 shows further detail of the transition section.

FIGS. 3-8 illustrate various aspects of the guidewire. FIG. 3 shows a schematic view of an outer sheath of a guidewire, comprising a proximal section 40, a transition section 42, and a distal section 44. The proximal section 40 is formed of a spun coil which has a tight pitch and is substantially gapless. An example of such a coil is an HHS® (Helical Hollow Strand) Tube obtainable from Fort Wayne Metals of Fort Wayne, Ind., USA. A suitable tube can be formed from a single layer of 304V Spring Temper stainless steel filament(s) of approximately 0.029 cm thickness to give a coil tube of approximately 0.17 cm OD. The proximal section 40 can have a bore that is substantially unobstructed so as to give substantially consistent torque transmission and bending capability along its length. The distal section 44 is formed from a wound coil, such as 304V Spring Temper stainless steel wire of approximately 0.025 cm thickness. A short section 46 near the distal end of the distal section 44 is wound at a looser pitch so as to provide a highly flexible region as is shown in FIG. 4. The proximal and distal sections 40, 44 are connected to each other by means of the transition section 42. FIG. 5 shows the transition section 42 in more detail. The transition section 42 comprises a substantially cylindrical main body 48 having proximal and distal extensions 50, 52 extending coaxially from opposite ends. The extensions 50, 52 are of reduced OD compared to the OD of the main body 48 and are sized to fit inside the respective bores of the proximal and distal sections 40, 44. The OD of the main body 48 is substantially the same as that of the proximal and distal sections 40, 44. The transition section can also be made from stainless steel and connected to the proximal and distal sections by welding. A deviation can be provided in the transition section 42 so that the outer coil tube is naturally in a slightly bent configuration.

A hub 54 is affixed at the proximal end of the proximal section 40 by which a user can apply torque to the guidewire. The hub can be permanently affixed, such as by gluing, or can be removable. A ball 56 can be welded to the distal end of the distal section 44 to provide an atraumatic surface. The proximal section 40 can also include a marker section 58 to assist a user in determining the extend of insertion of the guidewire into a delivery system.

Figure 6:
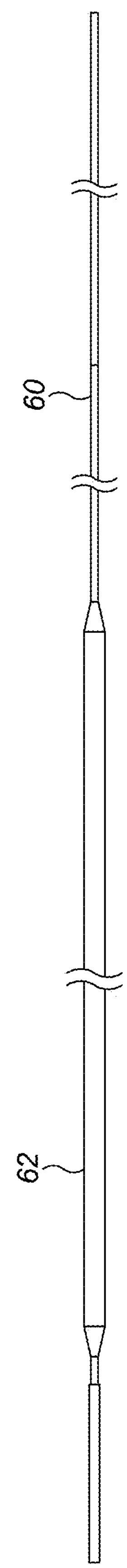
FIG. 6 shows further detail of the distal end of the core.
Figure 7:
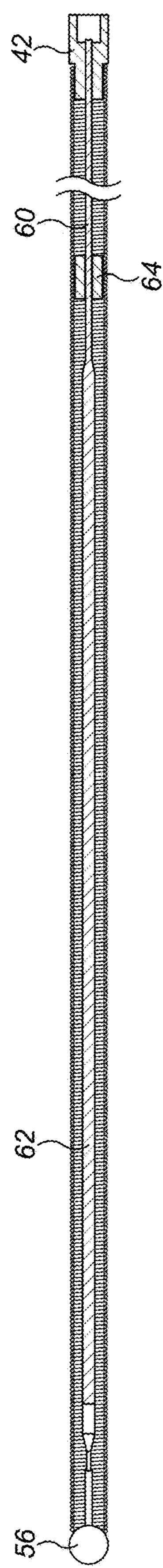
FIG. 7 shows the distal sheath section, the core, and the transition section.
Figure 8:
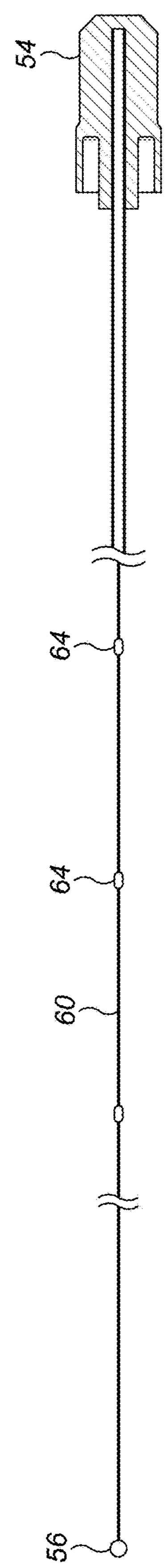
FIG. 8 shows further detail of the core.

A core is provided inside the coil forming the distal section 44, as shown in FIGS. 6 and 7. The core is formed of a wire 60 that is connected at one end in a bore 61 in the distal extension 52 of the transition section 42, and at the other end is a bore in the ball 56. The wire 60 is substantially cylindrical at its ends, but has been flattened to a thickness of about half of the original wire diameter at a position 62 close to the proximal end so that it will preferably bend in a direction perpendicular to the plane of the flattened section and assist in steering the end in use. As is shown in FIG. 8, a series of markers 64 are positioned along the core between the transition section 42 and the flattened section 62. The markers can be made of a material visible in a fluoroscopic imaging system, such as Pt/Ir.

In the configuration shown in these figures, distal section 44 is approximately half as long as the proximal section. The overall length can be of the order of 120 cm, although other lengths and ratios can be used according to requirements.

FIGS. 9-15 illustrate systems and methods using the guidewire described above.

Figure 9:
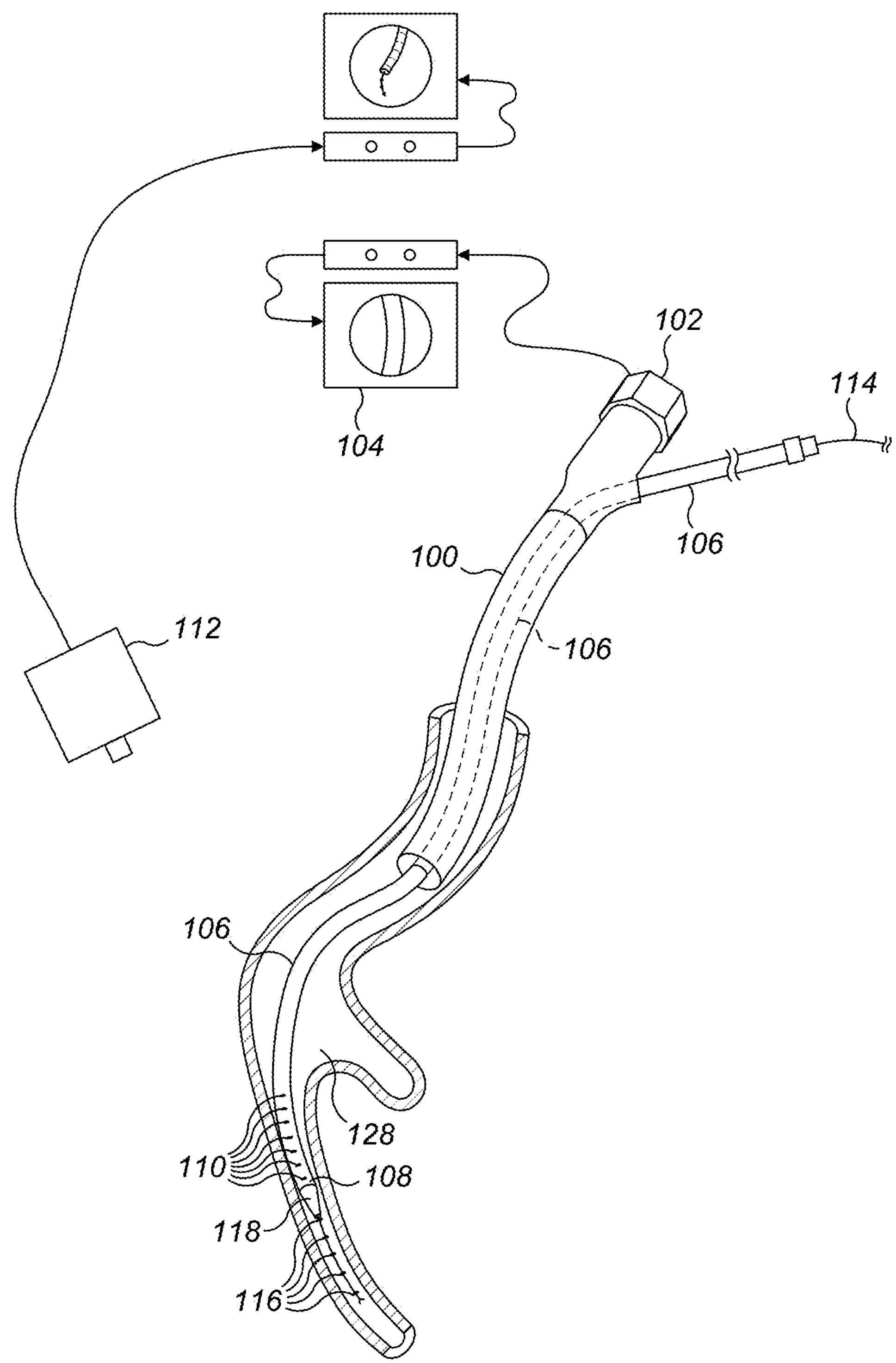
FIG. 9 shows a system for placing a lung volume reduction implant.

The system of FIG. 9 comprises a bronchoscope including a bronchoscope catheter 100 having a camera 102 at its distal end connected to a video processing system 104. A delivery catheter 106 extends through the lumen of the bronchoscope catheter 100. The distal end 108 of the delivery catheter 106 is provided with markers 110 visible to a fluoroscopic imaging system 112. A guidewire 114 of the type described above extends through the lumen of the delivery catheter 106 and can be advanced out of the distal end 108. The end of the guidewire 114 also has markers 116 (corresponding to markers 64 described above). A dilator 118 can be provided to endure a smooth transition between the outer surface of the guidewire 114 and the outer surface of the delivery catheters 106.

Figure 10:
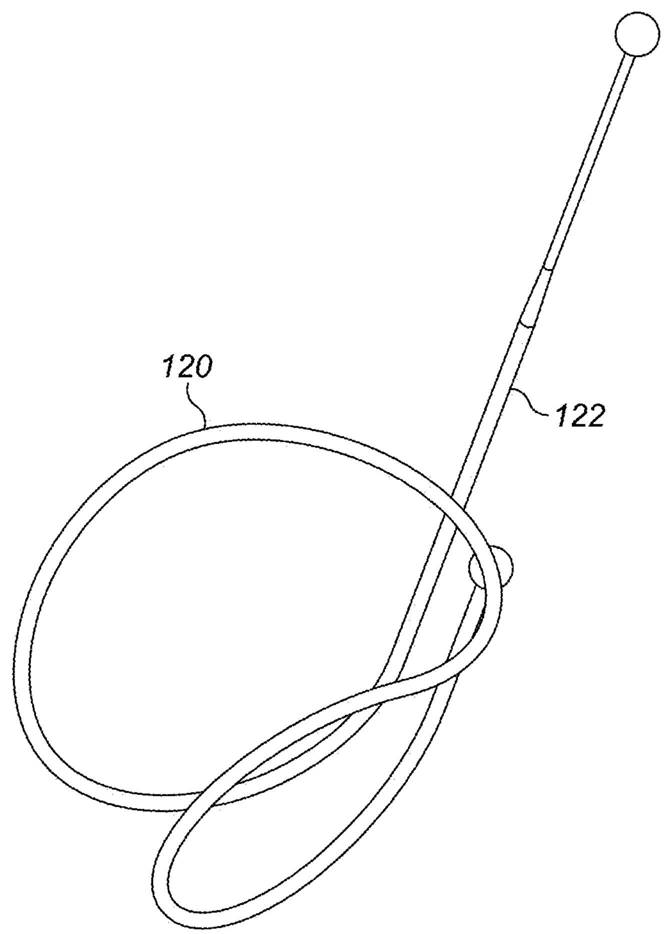
FIGS. 10 and 11 show details of an implant.
Figure 11:
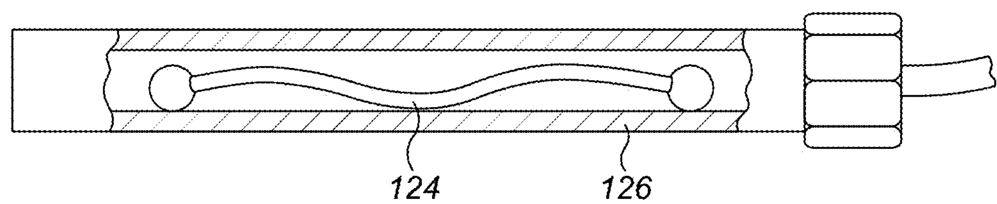

The system of FIG. 9 is intended for use with an implant of the type shown in FIGS. 10 and 11, although other shapes may also be used. In its normal state, the implant comprises an elongate member 120 that adopts a complex shape 122 comprising a series of curved sections, each curve centered on a separate axis. The implant 120 can be made from Nitinol wire and can have atraumatic terminals at the ends and one or more length markers (not shown). For delivery, the implant 120 is distorted into a relatively straight configuration 124 and constrained in a delivery cartridge 126.

In use, the bronchoscope catheter 100 of FIG. 9 is advanced into the upper airways of a patient either to the extent of its available length, or until its physical size prevents further insertion without damage to the lung tissue. The delivery catheter 106, together with the guidewire 114, is advanced through the lumen of the bronchoscope catheter and into the airway. The guidewire 114 is then further advanced along the delivery catheter 106 from the proximal end so as to extend from the distal end 108 and project further into the airway. The mark 58 can be positioned so as to indicate when the distal end of the guidewire 114 is at the distal end of the catheter 108. As the guidewire 114 is advanced further, it can be steered by applying a torque to the hub 54, the deviation allowing the distal end to be pointed in a required direction and the flexible section 46 and flattened core section 62 allowing the end to be eased into the required airway on contact with the wall of the airway. Progress can be monitored either via the viewing field of the bronchoscope, or by use of the remote fluoroscopic imaging system 112 once the end has passed out of this field of view. The deployment catheter 106 can be advanced with the guidewire 114 until its distal end 118 is at or near the distal end of the guidewire 114 in the airway of interest.

The proximal section 40 is not configured to extend beyond the distal end 118 of the delivery catheter 106. Consequently, the proximal section 40 can be configured for axial compression and torque transmission, together with the necessary degree of flexibility to be fed into the bronchoscope catheter 100. In the example described above, this is achieved using the tight pitch spun coil structure for the proximal section 40. By avoiding the need for the core 60 to extend to the hub 54, the proximal section 40 can be more flexible than the previously proposed structure and so provides for easier insertion into the catheter 106. The marker 58 can be positioned so as to indicate that the distal end of the guidewire 114 is at or near the distal end 118 of the delivery catheter 106, indicating to the user that further progress must be monitored using one or other of the imaging systems 104, 112.

By providing an asymmetry in the guidewire construction, such as a deviation at the transition section 42, the distal end can be directed off axis. This, together with the flexible region 46 and the flattened portion 62 of the core 60 means that when the distal end reaches an airway junction 128, torque can be applied at the hub 54 to cause the distal end to move radially in the airway, the flattened section 62 providing for preferential bending in the plane perpendicular to the plane of the flattened section 62. The provision of the atraumatic ball 58 and flexible end 46 mean that the airway tissue can provide a reaction surface to allow control of the position without damage to the tissue.

Figure 12:
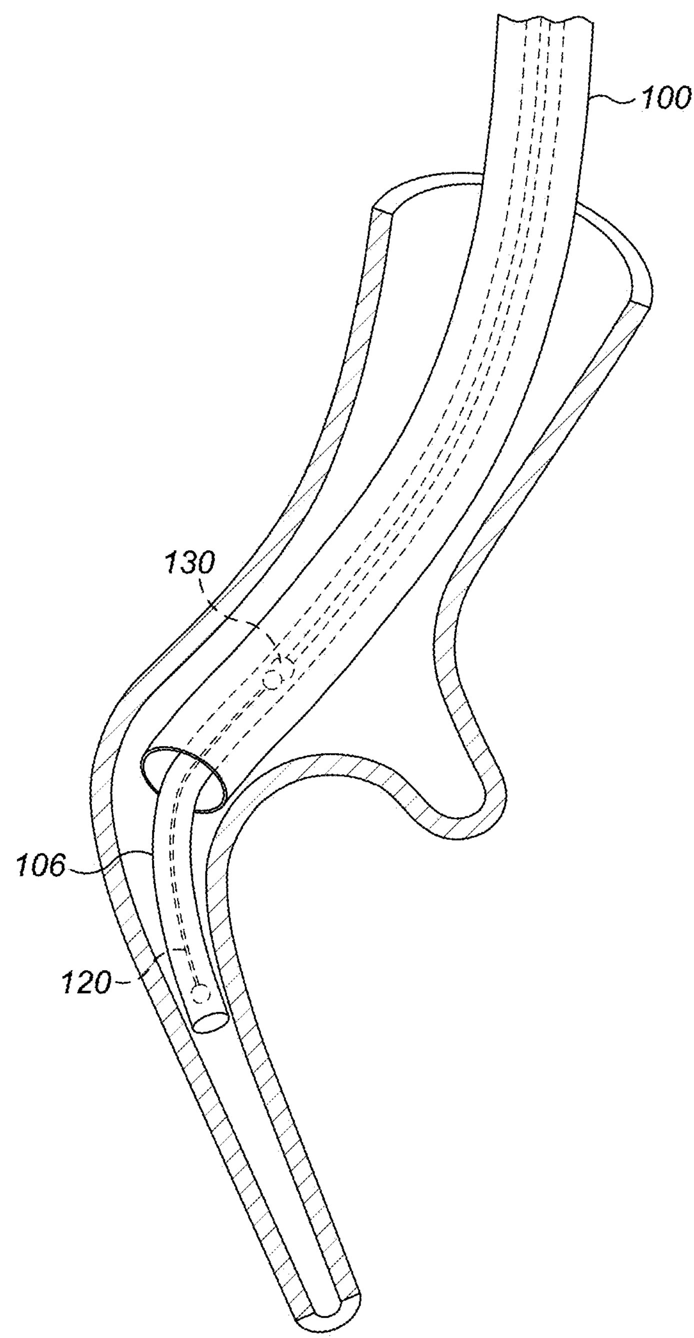
FIG. 12 illustrates delivery of the implant.
Figure 13:
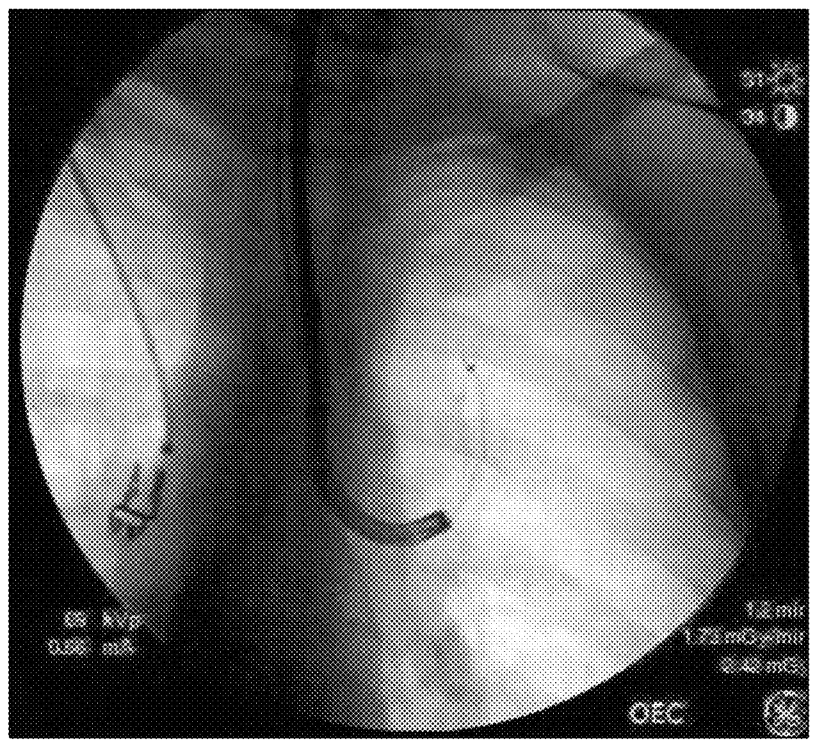
FIG. 13 shows a fluoroscopic image of an implant in the position illustrated in FIG. 12.
Figure 14:
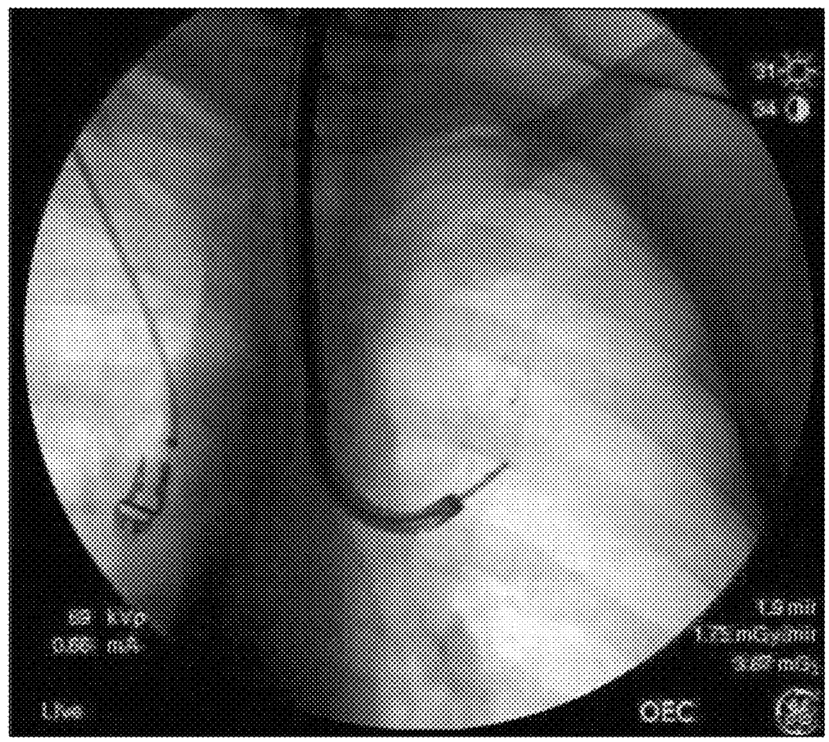
FIG. 14 shows a fluoroscopic image of an implant in a lung as the delivery catheter is removed.
Figure 15:
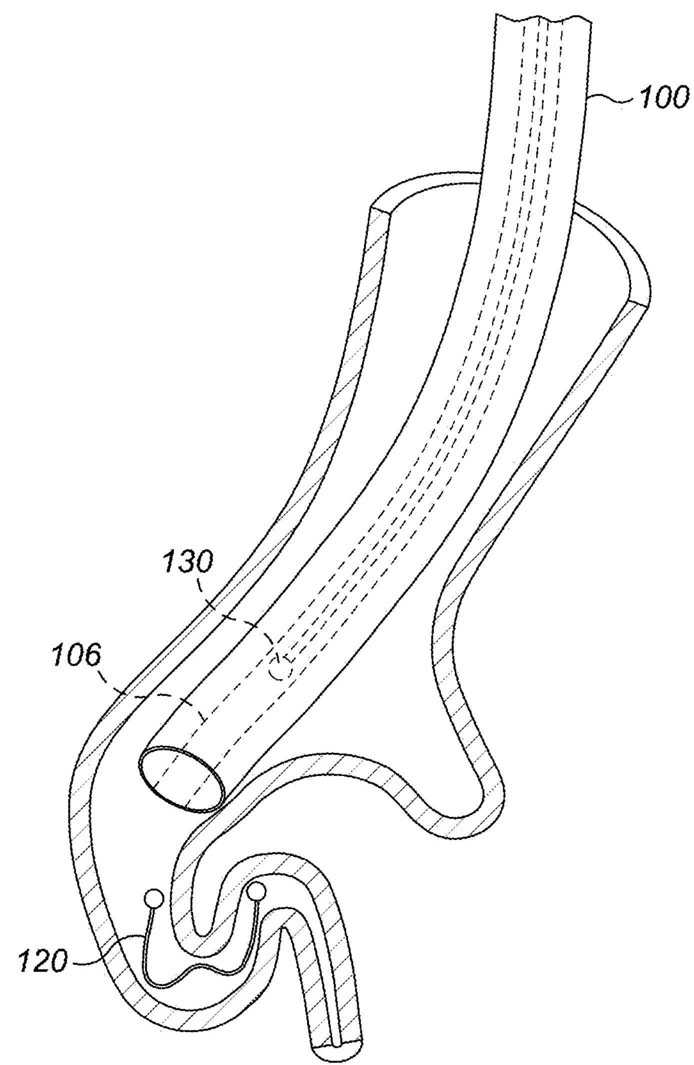
FIG. 15 illustrates the system after delivery of the implant.

Once the delivery catheter 106 is in position, it can be secured and the guidewire 114 withdrawn from the delivery catheter 106. The cartridge 126 carrying the implant 120 can then be connected in its place, and the implant 120 advanced along the delivery catheter 106 by a pusher device having a detachable connector 130 as shown in FIG. 12. FIG. 13 shows remote imaging system view of the implant 120 at the end of the delivery catheter 106. The implant 120 is held in place by the pusher device 130 and the delivery catheter 106 is withdrawn, allowing the implant 120 to return to its as-manufactured shape (FIG. 14), reducing the volume of lung tissue in that region as it does so. Once the implant 120 is completely outside the delivery catheter 106, the connector 130 is detached (FIG. 15) and the bronchoscope and delivery catheters 100, 106 can be withdrawn from the lung.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

In the previous description, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A guidewire, comprising:

an outer sheath having a proximal end and a distal end, and comprising a proximal section, a transition section, and a distal section, wherein the transition section is a body having a distal pin extension and a proximal pin extension, wherein:

the proximal pin extension has a first outer diameter, the distal pin extension has a second outer diameter, and the transition section comprises a main body having a third outer diameter, the third outer diameter being greater than the first and second outer diameters;

wherein an end of the proximal section is fixed to the proximal pin extension, and an end of the distal section is fixed to the distal pin extension of the transition section, and wherein the distal pin extension of the transition section comprises a first bore for receiving a proximal end of an inner core; and wherein the proximal end of the inner core is fixed within the first bore of the transition section, and wherein a distal end of the inner core is fixed to the distal end of the outer sheath.

2. The guidewire as claimed in claim 1, wherein the proximal section of the outer sheath defines a second bore extending from the proximal end of the outer sheath to the transition section.

3. The guidewire as claimed in claim 2, wherein the second bore of the proximal section of the outer sheath is substantially unobstructed between the proximal end of the outer sheath and the transition section.

4. The guidewire as claimed in claim 1, wherein the proximal section of the outer sheath and the distal section of the outer sheath comprise coils.

5. The guidewire as claimed in claim 4, wherein the coil comprising the proximal section of the outer sheath has different mechanical properties to the coil comprising the distal section of the outer sheath.

6. The guidewire as claimed in claim 5, wherein the coil comprising the proximal section of the outer sheath is a spun coil configured for torque transmission.

7. The guidewire as claimed in claim 4, wherein the transition section comprises an adapter to which the coils comprising the proximal and distal sections of the outer sheath are fixed.

8. The guidewire as claimed in claim 7, wherein the transition section comprises a cylindrical body, and wherein the proximal pin extension is configured for insertion into an open end of the coil comprising the proximal section of the outer sheath, and wherein the distal pin extension is configured for insertion into an open end of the coil comprising the distal section of the outer sheath.

9. The guidewire as claimed in claim 1, wherein the distal end of the outer sheath and the distal end of the inner core are fixed to a ball structure.

10. The guidewire as claimed in claim 1, wherein the inner core comprises a wire having proximal and distal ends and a flattened portion intermediate the proximal and distal ends of the wire.

11. The guidewire as claimed in claim 10, wherein the proximal and distal ends of the wire have substantially the same diameter.

12. The guidewire as claimed in claim 1, wherein the outer sheath is dimensioned to pass through a catheter for introduction into an airway of a lung of a patient.

13. The guidewire as claimed in claim 1, further comprising an end fitting connected to the proximal end of the proximal section and configured to allow a user to apply torque to the proximal section.

14. The guidewire as claimed in claim 13, wherein the end fitting comprises a hub that is permanently connected to the proximal end of the proximal section.

15. The guidewire as claimed in claim 13, wherein the end fitting comprises a hub that is removably connected to the proximal end of the proximal section.

16. The guidewire as claimed in claim 1, wherein the main body of the transition section is cylindrical.

17. A system comprising a first catheter, a guidewire according to claim 1, and a second catheter, wherein the first catheter is configured for introduction into a major airway of a lung of a patient, the guidewire is configured to be advanced from a lumen of the first catheter and further into a predetermined airway in the lung of the patient, and the second catheter is configured to be advanced through the lumen of the first catheter and over the guidewire into the predetermined airway of the lung of the patient.

18. The system as claimed in claim 17, further comprising an implant configured for delivery through a lumen in the second catheter and deployment into the predetermined airway of the lung of the patient.

19. A method of deploying a lung volume reduction implant into a predetermined airway of a lung of a patient using a system as claimed in claim 18, comprising:

advancing the first catheter and the guidewire into a major airway of the lung;

advancing the second catheter and guidewire through the lumen of the first catheter;

advancing the guidewire from the lumen of the second catheter and directing the distal end of the guidewire further into the predetermined airway by rotating the proximal end of the outer sheath so as to point the distal end of the outer sheath in the direction of the predetermined airway;

withdrawing the guidewire from the second catheter; and advancing a lung volume reduction implant through the lumen of the second catheter and deploying the implant into the predetermined airway.

20. A system comprising:

a first catheter configured for introduction into a major airway of a lung of a patient;

a second catheter configured to be advanceable through a lumen of the first catheter and further into a predetermined airway in the lung of the patient; and a guidewire according to claim 1, configured to be advanced through a lumen of the second catheter and further into the predetermined airway, wherein the second catheter is configured to be further advanceable over the guidewire and further into the predetermined airway of the lung of the patient.

21. The system as claimed in claim 20, further comprising an implant configured for delivery through a lumen in the second catheter and deployment into the predetermined airway of the lung of the patient.

22. A method of deploying a lung volume reduction implant into a predetermined airway of a lung of a patient using a system as claimed in claim 21, comprising:

advancing the first catheter into a major airway of the lung;

advancing the second catheter and guidewire through the lumen of the first catheter so as to extend into a predetermined airway of the lung;

further advancing the guidewire from the lumen of the second catheter and directing the distal end of the guidewire further into the predetermined airway by rotating the proximal end of the outer sheath so as to point the distal end of the outer sheath in the direction of the predetermined airway;

further advancing the second catheter over the guidewire further into the predetermined airway;

withdrawing the guidewire from the second catheter; and advancing a lung volume reduction implant through the lumen of the second catheter and deploying the implant into the predetermined airway.

* * * * *